United States Patent
Venkataraman

(12) 
(10) Patent No.: US 6,509,492 B1
(45) Date of Patent: Jan. 21, 2003

(54) TANNATE COMPOSITIONS AND METHODS OF TREATMENT

(75) Inventor: Balaji Venkataraman, Roswell, GA (US)

(73) Assignee: First Horizon Pharmaceutical Corporation, Alpharetta, GA (US)

( * ) Notice: Subject to any disclaimer, the term of this patent is extended or adjusted under 35 U.S.C. 154(b) by 6 days.

(21) Appl. No.: 09/952,711

(22) Filed: Sep. 14, 2001

Related U.S. Application Data

(60) Provisional application No. 60/316,548, filed on Aug. 31, 2001.

(51) Int. Cl.$^7$ .............................................. C07C 69/88
(52) U.S. Cl. ...................... 560/68; 514/226.5; 514/277; 514/290; 514/325; 514/568; 514/653
(58) Field of Search .................. 560/68; 574/226.5, 574/577, 290, 568; 514/226.5, 277, 290, 568, 653

(56) References Cited

U.S. PATENT DOCUMENTS

| | | |
|---|---|---|
| 2,950,309 A | 8/1960 | Cavallito |
| 3,282,789 A | 11/1966 | Marty et al. |
| 4,309,989 A | 1/1982 | Fahim |
| 4,619,934 A | 10/1986 | Sunshine et al. |
| 4,749,697 A | 6/1988 | Sunshine et al. |
| 4,749,711 A | 6/1988 | Sunshine et al. |
| 4,749,721 A | 6/1988 | Sunshine et al. |
| 4,749,722 A | 6/1988 | Sunshine et al. |
| 4,749,723 A | 6/1988 | Sunshine et al. |
| 4,767,402 A | 8/1988 | Kost et al. |
| 4,839,354 A | 6/1989 | Sunshine et al. |
| 5,025,019 A | 6/1991 | Sunshine et al. |
| 5,164,398 A | 11/1992 | Sims et al. |
| 5,599,846 A | 2/1997 | Chopdekar et al. |
| 5,614,178 A | 3/1997 | Bloom et al. |
| 5,663,415 A | 9/1997 | Chopdekar et al. |
| 5,759,579 A | 6/1998 | Singh et al. |
| 6,037,358 A | 3/2000 | Gordziel |
| 6,117,452 A | 9/2000 | Ahlgren et al. |
| 6,287,597 B1 | 9/2001 | Gordziel |
| 6,306,904 B1 * | 10/2001 | Gordziel |

FOREIGN PATENT DOCUMENTS

| | | |
|---|---|---|
| EP | 43738 B1 | 10/1985 |

* cited by examiner

*Primary Examiner*—Paul J. Killos
(74) *Attorney, Agent, or Firm*—Leydig, Voit & Mayer, Ltd.

(57) ABSTRACT

The present invention is directed to methods and compositions for treating upper respiratory indications, such as the treatment, management or mitigation of cough, cold, cold-like symptoms, symptoms related to upper respiratory infections, influenza symptoms and allergic rhinitis, perennial rhinnitis, nasal and Eustachian tube congestion in an animal by administration of tannate compositions comprising combinations of at least one or more agents into a single administrative dose.

4 Claims, No Drawings

TANNATE COMPOSITIONS AND METHODS OF TREATMENT

RELATED APPLICATIONS

The present application claims the benefit of U.S. Provisional Patent Application 60/316,548, filed Aug. 31, 2001.

TECHNICAL FIELD

The present invention is directed to methods and compositions for the treatment of symptoms of upper respiratory conditions, including allergic rhinitis, coryza, influenza, rhinovirus and other viral infections. More particularly the invention relates to tannate compositions comprising at least two or more agents for the treatment of upper respiratory indications, wherein the agents are provided in a single administrative dose.

BACKGROUND OF THE INVENTION

Upper respiratory symptoms, resulting from a cold or influenza infection or allergic reactions, though not generally life threatening are some of the most annoying symptoms to have. Work days and hours are lost when employees are debilitated by these symptoms. The symptoms include nasal congestion, cough, sinusitis, cough, cold, cold-like symptoms, influenza symptoms and allergic rhinitis. Additionally other symptoms of upper respiratory mucosal congestions such as those seen in perennial and rhinnitis and Eustachian tube congestion.

These symptoms are treated with a variety of therapeutic agents. For example, antihistamines interact with histamine released in the body in an allergic reaction by competing for the histamine $H_1$-receptor. Antihistamines reduce the effects of histamine in allergic reactions and tissue injury response. Antihistamines offset the histamine effects of increased capillary permeability and edema formation, particularly in the nasal mucosa where vascular engorgement, mucosa edema, irritation, sneezing and watery secretions result from histamine release.

Nasal decongestants act by release of adrenergic mediators from postganglionic nerve terminals. Ideally, nasal dcongestants are not given in amounts that cause other sympathomimetic effects such as pressor activity and central nervous system stimulation. The relief of symptoms of upper respiratory symptoms is achieved by the vasoconstriction and shrinkage of the nasal mucosa. Use of vasoconstriction produces a sustained, gradual decongestant effect with little if any return to congested levels seen prior to administration of the decongestant. Orally administered decongestants can reach mucosa that is not accessible by topical agents and allows for shrinkage of swollen tissues in the upper respiratory tract.

What is needed are methods and compositions comprising effective amounts of compositions of one or more therapeutic agents that are used for treatment of upper respiratory symptoms.

SUMMARY OF THE INVENTION

The present invention is directed to methods and compositions for treating upper respiratory indications in humans and animals, both adult and juvenile, comprising administration of compositions comprising one or more therapeutic agents. Such therapeutic agents include, but are not limited to, therapeutically effective amounts of tannate compositions, preferably antihistamines, cough suppressants or antitussives, decongestants and expectorants. Preferably the combinations are in single compositions comprising at least one or more agents, in pharmaceutical formulations. Methods and compositions are provided for the treatment of upper respiratory indications. The compositions are preferably formulated in the form of tablets, capsules, sterile solutions or suspensions, compounded in a conventional manner with physiologically acceptable vehicles or carriers, recipients, binders, preservatives, stabilizers, flavorings, or the like, as called for by accepted pharmaceutical practice.

Preferably, tannate compositions of the present invention comprise antihistamines, decongestants, cough suppressants or antitussives and expectorants. Such compositions can be used in combination with compounds from the same pharmacological class that do not contain tannates. Additionally, the compositions may comprise other therapeutic agents, for example, analgesics, narcotics, antibiotics, antivirals and antifungals.

The present invention is directed to compositions comprising tannate compounds and methods of use of such compositions. The present invention comprises pharmaceutical compositions comprising one or more of the following therapeutic agents in combination. Therapeutic agents of the present invention comprise antihistamines, sympathomimetic drugs such as nasal decongestants, bronchodilators, cough suppressants or antitussives and expectorants. Such therapeutic agents are administered for the treatment, management or mitigation of cough, cold, cold-like symptoms, symptoms related to upper respiratory infections, influenza symptoms and allergic rhinitis. Additionally other symptoms of upper respiratory mucosal congestions are included, such as those seen in perennial rhinitis, and for the relief of nasal congestion and Eustachian tube congestion. The compositions of the present invention may also be administered concurrently or sequentially with antibiotics, antiviral agents and analgesic compositions.

The present invention comprises injectable and noninvasive routes for delivery, including but not limited to, the oral, nasal, pulmonary, rectal, buccal, vaginal, transdermal and ocular routes. Compositions comprising combinations of at least two or more therapeutic agents may be administered through these routes of administration in compositions that allow for immediate or sustained release, controlled release or time-release dosing to the patient. The release profile of the compositions of the present invention allows for greater safety in administration of multiple agents, reduces the number of factors a physician must consider in treating upper respiratory indications with a multiple agent regimen, provides for greater compliance in patients, and results in fewer side effects for patients.

While studies have demonstrated a benefit of multi-drug therapy, the tasks of administering several different agents proves to be a challenge for the physician, patients, and caregivers. The present invention provides compositions and methods for treatment of upper respiratory indications by the administration of compositions comprising a combination of at least one or more therapeutic agents in an effective amount to treat the symptoms of upper respiratory indications.

The present invention provides compositions and methods for administering compositions comprising combinations of two or more therapeutic agents in compositions that are easily administered to persons having upper respiratory indications including but not limited to viral infection symptoms, cold symptoms, allergic rhinitis or other allergic reactions, runny nose, cough, post-nasal drip, nasal congestion and sinusitis. The present invention also provides compositions and methods for administering compositions comprising combinations of two or more therapeutic agents that promote high patient acceptance and compliance in persons with upper respiratory indications. The present invention provides compositions and methods for administering compositions comprising combinations of two or more therapeutic agents that maximize agent absorption in persons having upper respiratory indications.

These and other features and advantages of the present invention will become apparent after a review of the following detailed description of the disclosed embodiments and the appended claims.

DETAILED DESCRIPTION

The present invention is directed to methods and compositions for treatment of upper respiratory conditions. These conditions include, but are not limited to, indications including but not limited to viral infection symptoms, cold symptoms, allergic rhinitis or other allergic reactions, runny nose, cough, post-nasal drip, nasal congestion and sinusitis. Additionally other symptoms of upper respiratory mucosal congestion are included, such as those seen in perennial and allergic rhinitis, and for the relief of nasal congestion and Eustachian tube congestion. Preferred methods of treatment include the administration of compositions comprising combinations of at least one or more agents in an effective amount to treat symptoms of these conditions. Compositions comprise combinations of at least one or more agents comprising antihistamines, decongestants, cough suppressants and expectorants. Additionally, the compositions can comprise other therapeutic agents such as analgesics, narcotics, antibiotics, antifungals, antimycoplama agents and antiviral agents. The methods of the present invention comprise routes of administration that include, but are not limited to, oral, buccal, nasal, transdermal, injectable, slow release, controlled release, iontophoresis, sonophoresis, and other delivery devices and methods. Injectable methods include, but are not limited to, parenteral routes of administration, intravenous, intramuscular, subcutaneous, intraperitoneal, intraspinal, intrathecal, intracerebroventricular, intraarterial and other routes of injection. The methods include a frequency of administration that is dependent upon the patient condition, method of administration and concentration of the therapeutic agent.

Additionally, the present invention comprises compositions that provide formulations for controlled, slow release, or sustained release of the therapeutic compounds over a predetermined period of time. Methods of administration of compositions comprising at least one or more agents using these formulations allow for a desired concentration of these agents to be maintained in the bloodstream of the patient for a longer period of time than with conventional formulations. Slow release, controlled or sustained release formulations are known to those skilled in the art and include formulations such as coated tablets, pellets, capsules, dispersion of the therapeutic agent in a medium that is insoluble in physiologic fluids or where the release of the therapeutic agent is released after degradation of the formulation due to mechanical, chemical or enzymatic activity, or is released from an implantable device.

It is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting.

Definitions

It must be noted that, as used in this specification and the appended claims, the singular forms "a," "an," and "the" include plural referents unless the context clearly dictates otherwise. Thus, for example, reference to a bilayer tablet containing "compositions comprising combinations of two or more agents" may include a mixture of such compositions, reference to "an adhesive" includes reference to one or more of such adhesives, and reference to "a bile salt" includes reference to a mixture of two or more of such bile salts.

The term "treating" "treatment" "treat" as used herein includes preventative, emergency, and long-term treatment.

The term "multi-agent compound" includes any compositions comprising combinations of at least two or more agents for administration to patients to treat medical conditions.

The terms "drug", "agent", "therapeutic agent", "medication", and the like are considered to be synonymous and all refer to the component that has a physiological effect on the individual to whom the composition is administered.

As used herein, "chemical enhancer," "penetration enhancer", "permeation enhancer," and the like shall be inclusive of all enhancers that increase the flux of a permeant, agent, or other molecule across the mucosa and is limited only by functionality. In other words, all cell envelope disordering compounds, solvents, steroidal detergents, bile salts, chelators, surfactants, non-surfactants, fatty acids, and any other chemical enhancement agents are intended to be included.

Permeation enhancers are comprised of two primary categories of components, i.e., cell-envelope disordering compounds and solvents or binary systems containing both cell-envelope disordering compounds and solvents. As discussed above, other categories of permeation enhancer are known, however, such as steroidal detergents, bile salts, chelators, surfactants, non-surfactants, and fatty acids.

Cell envelope disordering compounds are known in the art as being useful in topical pharmaceutical preparations and function also in agent delivery through the skin or mucosa. These compounds are thought to assist in dermal penetration by disordering the lipid structure of the stratum corneum cell-envelopes. A list of such compounds is described in European Patent Application 43,738, published Jun. 13, 1982, which is incorporated herein by reference. It is believed that any cell envelope disordering compound is useful for purposes of this invention.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted alkyl-azacycloalkyl-2-ones (azones) and the like.

As used herein, "bile salts" means steroidal detergents that are the natural or synthetic salts of cholanic acid, e.g. the salts of cholic and deoxycholic acid or combinations of such salts, and the unionized acid form is also included. Bile salt analogs having the same physical characteristics and that also function as permeation enhancers are also included in this definition.

As used herein, "transmucosal," "transbuccal," and similar terms mean passage of a multi-agent composition into and through the mucosa to achieve effective therapeutic blood levels or deep tissue levels.

As used herein, "effective amount" means an amount of a multi-agent composition that is sufficient to provide a selected effect and performance at a reasonable benefit/risk ratio attending any medical treatment. An effective amount of a permeation enhancer, as used herein, means an amount selected so as to provide the selected increase in permeability and, correspondingly, the desired depth of penetration, rate of administration, and amount of agent delivered.

As used herein, "single administrative dose" means that the therapeutic agents are combined in a composition that is provided to the individual in one administration. The individual agents are provided in the composition at the desired concentration for each agent and the composition may be administered as many times a day to the patient as is necessary.

As used herein, "adhesive," "adhesive polymer", "mucoadhesive", or such similar terms refers to hydrophilic polymers, natural or synthetic, which, by the hydrophilic designation, can be either water soluble or swellable and which are compatible with the enhancers and compositions comprising two or more agents combined. Such adhesives function for adhering the dosage forms to the mucous tissues of the oral cavity, such as the gingiva. Such adhesives are inclusive of hydroxypropyl cellulose, hydroxypropyl methylcellulose, hydroxy ethylcellulose, ethylcellulose, carboxymethyl cellulose, dextran, guar gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and mixtures thereof and the like.

By "system", "drug delivery system", "transmucosal delivery system" or the like is meant a unit dosage form of a drug or agent composition, preferably any compositions comprising combinations of at least two or more agents, including carriers, enhancers, and other components, in which the multi-agent compound is contained in or accompanied by means for maintaining the drug composition in a drug transferring relationship or providing any multi-agent compounds to the desired site in the body. Such means can be either a patch, tablet, troche, or other device of determined physical form for continuous agent administration thereto for systemic transport, or such means can be formulated in free form to be applied directly to the patient as a cream, gel, gum, ointment and the like.

The term "troche" includes pastille, lozenge, morsulus, rotula, trochiscus, and the like.

"Free form" means that the formulation is spreadable or malleable into a selected shape at the time of application.

"Determined physical form" means that the formulation has a form determined by a device. The means used may be a device such as a tablet or matrix patch or liquid reservoir patch. A matrix patch contains the agent, permeation enhancer, and other optional ingredients suspended or dispersed in an adhesive layer. A reservoir patch contains the agent, permeation enhancer, and other optional ingredients in a reservoir, which can be in liquid form, or the liquid can be gelled or thickened by an agent such as mineral oil, petroleum jelly and various aqueous gelling agents and hydrophilic polymers. Such a reservoir or matrix patch is brought into contact with the surface and is held in place by a suitable adhesive. In a reservoir patch, the agent composition is applied to the surface through a permeable membrane forming the reservoir floor that is in direct contact with the surface.

The compositions of the present invention may further include pharmaceutically acceptable carriers. The compositions may also include other medicinal agents, pharmaceutical agents, carriers, adjuvants, diluents and other pharmaceutical preparations known to those skilled in the art. Such agents are known to those skilled in the art and are generally described as being biologically inactive and can be administered to patients without causing deleterious interactions with the therapeutic agent. Examples of carriers or excipients for oral administration include corn starch, lactose, magnesium stearate, microcrystalline cellulose and stearic acid, povidone, dibasic calcium phosphate and sodium starch glycolate. Any carrier suitable for the desired administration route is contemplated by the present invention.

The present invention comprises compositions and methods for the treatment of allergic and upper respiratory disorders and symptoms. The compositions of the present invention comprise tannate compounds. More particularly, the compositions comprise combinations of therapeutic agents from pharmacological classes such as antihistamines, sympathomimetics, decongestants, cough suppressants, antitussives and expectorants. The therapeutic agents are administered in effective amounts in pharmaceutical formulations comprising admixtures with suitable pharmaceutical diluents, excipients or carriers. The formulations may be in tablets, capsules, elixirs or syrups. Additionally, the formulations of the compositions of the present invention may comprise sustained release formulations that provide rate controlled release of any one or more of the therapeutic agents. Sustained release formulations are well known in the art.

It is believed that tannate salts of active agents provide therapeutic activity for longer time periods. In effect, the inclusion of an active agent in a tannate salt form extends the release profile of the active agent and there is less spiking in pharmacological effect of the active agent. This leads to better compliance by the patient in that the active agent in the tannate salt form does not need to be given as often and there are fewer side effects, particularly from over dosage effects.

The tannate compositions of the present invention can be made by methods known to those skilled in the art. Preparations of tannate compounds in a very pure form are taught in U.S. Pat. Nos. 5,599,846 and 5,663,415 to Chopdekar et al., which are herein incorporated in their entireties. In general, one method of making tannate compounds comprises reacting the base compound, such as chlorpheniramine or brompheniramine, with tannic acid in a solvent such as alcohol.

Tannate compositions of the present invention comprise pharmaceutical compositions including but not limited to, the tannate compounds listed in Table 1.

TABLE 1

| Therapeutic agents |
|---|
| Antihistamines |
| Azatadine tannate |
| Chlorpheniramine tannate |
| Brompheniramine tannate |
| Chlorcyclizine tannate |
| Dexchlorpheniramine tannate |
| Dexbrompheniramine tannate |
| Triprolidine tannate |
| Diphenhydramine tannate |
| Doxylamine tannate |
| Carbinoxamine tannate |
| Phenindamine tannate |
| Pyrilamine tannate |

TABLE 1-continued

Therapeutic agents

Thonzylamine tannate
Triprolidine tannate
Decongestants

Pseudoephedrine tannate
Phenylephrine tannate
Cough Suppressants/Antitussives

Dextromethorphan tannate
Expectorants

Guaifenesin tannate

The tannate compounds provide relief from upper respiratory tract symptoms depending upon the pharmacological class of compound used. For example, guaifenesin tannate is an expectorant, which is prescribed to loosen phlegm (mucus) and thin bronchial secretions to rid the bronchial passageways of bothersome mucus. It is effective for the temporary relief of symptoms associated with sinusitis, coryza, influenza, pharyngitis, bronchitis, common cold, perennial, seasonal, vasomotor allergic rhinitis. It is also effective for the temporary relief of cough associated with respiratory tract infections and related conditions such as sinusitis, pharyngitis, bronchitis, common cold, and asthma, when these conditions are complicated by tenacious mucus and/or mucus plugs. An expectorant such as guaifenesin tannate is used to promote nasal or sinus drainage and for the symptomatic relief of respiratory conditions characterized by dry nonproductive cough and in the presence of tenacious mucus and/or mucous pugs in the upper or lower respiratory tract. Guaifenesin tannate helps drainage of the bronchial tubes by thinning the mucus and temporarily controls cough due to minor throat and bronchial irritation as may occur with the common cold or inhaled irritants. Guaifenesin tannate helps loosen phlegm (mucus) and thin bronchial secretions which are then removed from the bronchial tubes, and makes a cough more productive. Use of guaifenesin tannate in the compositions of the present invention provides for the symptomatic relief of irritating non-productive cough associated with upper and lower respiratory tract congestion.

Antihistamines, another component therapeutic agent of the present invention, provide temporary relief of symptoms associated with coryza, colds, seasonal, perennial, or vasomotor allergic rhinitis (hay fever). For example, chlorpheniramine tannate, brompheniramine tannate and diphenhydramine tannate are also used for the treatment of allergic skin reactions of urticaria and angioedema. Antihistamines are used in the methods of treatment of the symptoms resulting from irritation of sinus, nasal and upper respiratory tract tissues. The present invention comprises compositions comprising antihistamines, for example, chlorpheniramine tannate, brompheniramine tannate and diphenhydramine tannate for decreasing the symptoms of itchy watering eyes, runny nose, itchy nose, post nasal drip and sneezing, which may be associated with an allergic-like response.

The present invention comprises compositions comprising antitussives, for example, dextromethorphane tannate. Antitussives provide temporary relief of cough due to minor throat and bronchial irritation as may occur with a cold, inhaled irritants, infections of the upper and lower respiratory tracts, perennial, seasonal or vasomotor allergic rhinitis. The present invention comprises compositions comprising antitussives, for example, dextromethorphane tannate for suppressing the cough control center and relieving coughing.

The present invention comprises compositions comprising anticholinergics, also known as antimuscarinics, for example, methoscopolamine tannate, for relieving rhinorrhea.

The present invention comprises compositions comprising single ingredient or combinations of two or more therapeutic agents for the treatment of viral infection symptoms, cold symptoms, allergic rhinitis or other allergic reactions, runny nose, cough, post-nasal drip, rhinorrhea and sinusitis. Additionally other symptoms of upper respiratory mucosal congestion are included, such as those seen in perennial rhinitis, and for the relief of nasal congestion and Eustachian tube congestion. Preferably, such compositions comprise single therapeutic agents or combinations of two or more therapeutic agents, such as antihistamines, decongestants, cough suppressants and expectorants. A preferred composition comprises at least one of an antihistamine, a decongestant, a cough suppressant and an expectorant, or a combination of one or more of these therapeutic agents, more preferably, compositions comprises tannate salts of one or more of an antihistamine, a decongestant, a cough suppressant and an expectorant. It is theorized that compositions comprising therapeutic agents of a uniform salt lead to compositions having fewer unwanted side effects. Such compositions may also optionally include analgesic agents or narcotic agents.

Administration of the therapeutic agents of the present invention is dependent on the route of administration and the formulation of the compositions, for example, whether the formulation is designed for quick release or long term release. The doses provided herein may be amended by those skilled in the art, such as physicians or formulation pharmacists. Doses may differ for adults from those for pediatric patients. Suggested dosage amounts for representative agents are given in Table 2. The doses in Table 2 are not to be seen as limiting to the methods and compositions of the present invention and are given in standard molecular compounds, which would be converted to equivalent tannate compounds. Table 3 shows a comparison of tannate compound dosages with other compounds.

TABLE 2

REPRESENTATIVE DOSAGES

| | Adult | | Pediatric | |
|---|---|---|---|---|
| Agent | Max Daily Dose | Oral Dose | Max Daily Dose | Oral Dose |
| Azatadine maleate | 4 mg | 1 mg$^2$ | | |
| Chlorpheniramine maleate | 24 mg | 4 mg$^3$ | 12 mg<br>6 mg$^1$ | 2 mg$^3$<br>1 mg$^3$ |
| Brompheniramine hydrobromide | 24 mg | 4 mg$^3$ | 12 mg<br>6 mg$^1$ | 2 mg$^3$<br>1 mg$^1$ |
| Chlorcyclizine HCl | 75 mg | 25 mg$^4$ | 37.5 mg<br>18.75 mg$^1$ | 12.5/6–8 h<br>6.25/6–8 h$^1$ |
| Dexchlorpheniramine maleate | 12 mg | 2 mg$^3$ | 6 mg<br>3 mg$^1$ | 1 mg$^3$<br>0.5 mg$^{3, 1}$ |
| Dexbrompheniramine maleate | 12 mg | 2 mg$^3$ | 6 mg<br>3 mg$^1$ | 1 mg$^3$<br>0.5 mg$^{3, 1}$ |

TABLE 2-continued

REPRESENTATIVE DOSAGES

| | Adult | | Pediatric | |
|---|---|---|---|---|
| Agent | Max Daily Dose | Oral Dose | Max Daily Dose | Oral Dose |
| Diphen-hydramine HCl/citrate | 456 mg | 38–76 mg$^3$ | 228 mg 37.5–57 mg$^1$ | 19–38 mg$^3$ 6.25–9.5 mg$^{3,\,1}$ |
| Doxylamine succinate | 75 mg | 7.5–12.5 mg$^3$ | 37.5 18.75 mg$^1$ | 3.75–6.25$^3$ 1.9–3.2 mg$^{3,\,1}$ |
| Phenind-amine tartrate | 150 mg | 12.5–25 mg$^3$ | 75 mg 37.5 mg$^1$ | 6.25–12.5$^3$ 6.25 mg$^{3,\,1}$ |
| Pheniramine maleate | 150 mg | 12.5–25 mg$^3$ | 75 mg 37.5 mg$^1$ | 6.25–12.5$^3$ 3.2–6.3 mg$^{3,\,1}$ |
| Pyrilamine maleate | 200 | 25–50 mg$^3$ | 100 50 mg$^1$ | 12.5–25 mg$^3$ 6.3–12.5 mg$^1$ |
| Thonzyl-amine HCl | 600 mg | 50–100 mg$^3$ | 300 mg 150 mg$^1$ | 25–50 mg$^3$ 12.5–25 mg$^1$ |
| Triproli-dine HCl | 10 mg | 2.5 mg$^3$ | 5 mg 2.5–4 mg$^1$ | 1.25 mg$^3$ 0.63–0.94 mg$^1$ |
| Pseudo-ephedrine HCl | 240 mg | 60 mg$^3$ | 120 mg 60 mg$^1$ | 30 mg$^3$ 15 mg$^{3,\,1}$ |
| Phenyl-ephrine HCl | 60 mg | 10 mg$^3$ | 30 mg 15 mg$^1$ | 5 mg$^3$ 2.5 mg$^{3,\,1}$ |
| Dextro-methorphan | 120 mg | 10–20 mg$^3$ | 60 30$^1$ | 5–10 mg$^3$ 2.5–5 mg$^1$ |
| Guaifenesin | 2400 mg | 200–400 mg$^3$ | 1200 600 mg$^1$ | 100–200 mg$^3$ 50–100 mg$^1$ |

$^1$Children. ages 2–6
$^2$every 12 hours
$^3$every 4–6 hr
$^4$every 6–8 hr

TABLE 3

Tannate Conversion Examples

| | |
|---|---|
| Pseudoephedrine HCL | 30 mg |
| Pseudoephedrine tannate | 82 mg |
| Chlorpheniramine maleate | 2 mg |
| Chlorpheniramine tannate | 3.2 mg |
| Dextromethorphan HBr | 10 mg |
| Dextromethorphan tannate | 17.5 mg |
| Guaifenesin | 200 mg |
| Guaifenesin tannate | 543 mg |
| Brompheniramine maleate | 3 mg |
| Brompheniramine tannate | 4.5 mg |
| Methscopolamine HBr | 0.624 mg |
| Methscopolamine tannate | 1.0 mg |

Preferred compositions of the present invention comprise single agent or combinations of multiple agents comprising one or more of an antihistamine, a decongestant, an expectorant and a nasal decongestant, or their functional equivalents, in pharmaceutically acceptable carriers, formulations or excipients. Single agents compositions comprise, but are not limited to, azatadine tannate, chlorpheniramine tannate, brompheniramine tannate, chlorcyclizine tannate, dexchlorpheniramine tannate, dexbrompheniramine tannate, triprolidine tannate, diphenhydramine tannate, doxylamine tannate, carbinoxamine tannate, phenindamine tannate, pheniramine tannate, pyrilamine tannate, thonzylamine tannate, triprolidine tannate, pseudoephedrine tannate, phenylephrine tannate, dextromethorphan tannate, diphenhydramine tannate and guaifenesin tannate.

Compositions comprising two or therapeutic agents of tannate salts preferably comprise two or more agents from differing pharmacological classes, though efficacious combinations of two or more therapeutic agents from the same pharmacological class are also contemplated by the present invention. Preferred tannate compositions comprising two or more pharmaceutical classes include an antihistamine and a decongestant; an antihistamine and an antitussive; an antihistamine and an expectorant; and antihistamine, a decongestant and an antitussive; and antihistamine, a decongestant, an antitussive and an expectorant; an antihistamine, an antitussive and an expectorant; a decongestant and an antitussive; a decongestant and an expectorant; a decongestant, an antitussive and an expectorant; an antitussive and an expectorant.

The present invention comprises methods of administration to animals, both adult and juvenile, of compositions to effectively treat symptoms associated with upper respiratory conditions. Methods of the present invention comprise administration of effective compositions for the treatment, management or mitigation of cough, cold, cold-like symptoms, symptoms related to upper respiratory infections, influenza symptoms and allergic rhinitis. Additionally other symptoms of upper respiratory mucosal congestions are included, such as those seen in perennial rhinitis, rhinorrhea, itchy water eyes, sinusitis, and for the relief of nasal congestion and Eustachian tube congestion. The methods comprise administration of compositions comprising tannate therapeutic agents, including, but not limited to, azatadine tannate, chlorpheniramine tannate, brompheniramine tannate, chlorcyclizine tannate, dexchlorpheniramine tannate, dexbrompheniramine tannate, triprolidine tannate, diphenhydramine tannate, doxylamine tannate, carbinoxamine tannate, phenindamine tannate, pheniramine tannate, pyrilamine tannate, thonzylamine tannate, triprolidine tannate, pseudoephedrine tannate, phenylephrine tannate, dextromethorphan tannate, diphenhydramine tannate and guaifenesin tannate. An efficacious amount of the tannate composition is administered to an animal, adult or juvenile, and preferred ranges of the amount of tannate composition administered is provided in Table 4. This table is not to be seen to be limiting to the present invention and is given in standard molecular compounds, which would be converted to equivalent tannate compounds. For example 30 mg pseudoephedrine hydrochloride when converted to the tannate molecule is equivalent to 75 mg pseudoephedrine tannate. Similarly, 15 mg dextromethorphan hydrobromide is equivalent to 10 mg dextromethorphan tannate.

TABLE 4

Preferred Ranges

| Agent | Preferred Ranges$^1$ | Agent | Preferred Ranges$^1$ |
|---|---|---|---|
| Azatadine maleate | 0.25 to 6 | Pyrilamine maleate | 1.5 to 300 |
| Chlorpheniramine maleate | 1 to 24 | Thonzylamine HCl | 4 to 800 |
| Brompheniramine tannate | 1 to 24 | Triprolidine HCl | .05 to 25 |
| Chlorcyclizine HCl | 5 to 100 | Pseudoephedrine HCl | 3 to 300 |
| Dexchlorpheniramine maleate | 0.1 to 25 | Phenylephrine tannate | 0.5 to 80 |
| Dexbrompheniramine maleate | 0.1 to 25 | Dextromethorphan hydrobromide | 0.5 to 200 |
| Diphenhydramine HCl | 3 to 600 | Methoscopolamine nitrate | 0.01 to 5 |
| Doxylamine succinate | 0.5 to 100 | Guaifenesin | 5 to 3000 |

TABLE 4-continued

Preferred Ranges

| Agent | Preferred Ranges[1] | Agent | Preferred Ranges[1] |
|---|---|---|---|
| Phenindamine taratrate | 2.5 to 200 | Pheniramine maleate | 1–200 |

[1]Approximate mg amounts per 24 hour.

Most preferred compositions of the present invention comprise the single therapeutic agent and combinations of two or more therapeutic agents in a liquid formulation are shown in Table 5.

TABLE 5

| Combination | Strength per 5 mL | Dosing |
|---|---|---|
| Pseudoephedrine tannate | 75–300 mg | 2–6 yrs: ½–1 tsp q 12 hrs<br>6–12 yrs: 1–2 tsp q 12 hrs<br>12 yrs–Up: 2–4 tsp q 12 hrs |
| Pseudoephedrine tannate | 75 mg | 2–6 yrs: ½–1 tsp q 12 hrs |
| Chlorpheniramine tannate | 6 mg | 6–12 yrs: 1–2 tsp q 12 hrs<br>12 yrs–Up: 2–4 tsp q 12 hrs |
| Pseudoephedrine tannate | 75 mg | 2–6 yrs: ½–1 tsp q 12 hrs |
| Guaifenesin tannate | 150-600 mg (standard guaifenesin molecule) | 6–12 yrs: 1–2 tsp q 12 hrs<br>12 yrs–Up: 2–4 tsp q 12 hrs |
| Pseudoephedrine tannate | 75 mg | 2–6 yrs: ½–1 tsp q 12 hrs |
| Chlorpheniramine tannate | 4.5 mg | 6–12 yrs: 1–2 tsp q 12 hrs<br>12 yrs–Up: 2–4 tsp q 12 hrs |
| Dextromethorphan tannate | 10–30 mg | q 12 hrs |
| Pseudoephedrine tannate | 75 mg | 2–6 yrs: ½–1 tsp q 12 hrs |
| Brompheniramine tannate | 3–6 mg[1] | 6–12 yrs: 1–2 tsp q 12 hrs<br>12 yrs–Up: 2–4 tsp q 12 hrs |
| Pseudoephedrine tannate | | 2–6 yrs: ½–1 tsp q 12 hrs |
| Chlorpheniramine tannate | 75 mg 4.5 mg | 6–12 yrs: 1–2 tsp q 12 hrs |
| Methscopolamine tannate | 0.625 mg[2] | 12 yrs–Up: 2–4 tsp q 12 hrs |

[1]Standard brompheniramine hydrobromide molecule
[2]Standard methoscopolamine nitrate molecule Other preferred compositions of the present invention comprise the therapeutic agents of more than one antihistamine and a decongestant, particularly chlorpheniramine tannate (4 mg/5 ml), brompheniramine tannate (3–6 mg/5 ml) and dextromethorphane tannate (10–30 mg/5 ml). Additional preferred composition comprise pseudoephedrine tannate (75 mg/5 ml), brompheneramine tannate (3–6 mg/5 ml) and methoscopolamine tannate (0.625 mg/5 ml). Preferred methods of administration comprise those provided in Table 5.

The routes of administration for agents is chosen according to the speed of absorption desired and the site of action of the agent. Some agents are formulated for a specific route only and must be given in that manner. Various routes of administration of the present invention are presented herein.

Oral and enteral administration require that the therapeutic agent not be destroyed by the environment of the stomach and digestive enzymes. This means is too slow if rapid absorption is required, and cannot be used if the patient is vomiting. Rectal administration in the form of liquids or suppositories circumvents this problem in enteral administration. Rectal suppositories can be prepared by mixing the agent with a suitable non-irritable vehicle, for example, cocoa butter and polyethylene glycol, which is in the solid state at ordinary temperatures, in the liquid state at temperatures in intestinal tubes Mucosal routes of administration other than the above include absorption through the nasal mucosa, the buccal mucosa, sublingually, or the bronchioles, the latter usually achieved through inhalation of an aerosol. Vaginal or rectal administration are also mucosal routes of agent.

Percutaneous administration is used for iontophoresis or by direct absorption through the skin. Iontophoreses is the electrically driven application of agents or medicants, in their ionic form, to the surface tissues of a patient. The application of electric current causes migration of ions into the tissue wherein such migration is proportional to the quantity of current applied through the iontophorectic system. Direct absorption can be from application of the agent to the skin surface by means of a cream.

Parenteral administration is used when an agent cannot be given by mouth. The speed of absorption varies greatly with the specific route used, which may be subcutaneous, intravenous, intramuscular, intra-arterial, intraperitoneal, intrathecal, intracardiac, or intrasternal.

The rate of absorption of an agent administered as a tablet or other solid oral-dosage form is partly dependent upon its rate of dissolution in the gastrointestinal fluids. This factor is the basis for the so-called controlled-release, extended release, sustained-release, or prolonged-action pharmaceutical preparations that are designed to produce slow, uniform absorption of the agent for 8 hours or longer. Potential advantages of such preparations are reduction in the frequency of administration of the agent as compared with conventional dosage forms resulting in improved compliance by the patient, maintenance of a therapeutic effect overnight, and decreased incidence and or intensity of undesired effects by elimination of the peaks in drug concentration that often occur after administration of immediate-release dosage forms.

The methods of administration of the present invention can vary within limits, but necessarily involve providing the selected compositions comprising combinations of at least two or more agents to the patient such that drug delivery is initiated and continues for a period of time sufficient to provide the selected pharmacological or biological response. The frequency of administration of treatment depends upon the patient condition, mode of delivery and concentration of therapeutic agent. Treatment can be delivered as often as needed (ql), four times daily (qid), daily (qd) or at certain times in a 24 hour cycle such as after eating or at bedtime.

Simple multi-agent compound agent delivery systems of the present invention comprise capsules containing differently coated pellets of the agent. On release from the capsule, the uncoated pellets provide an initial amount of the composition comprising the combination of two or more agents to the body, and the coated pellets provide the multi-agent composition over a period of time. Another system comprises a tablet made from a polymer containing the multi-agent compound dispersed within. As the polymer slowly degrades in the stomach, the multi-agent compound is released. Additional agent delivery systems include hydrogel materials with coated pills embedded in the hydrogel, such as that taught in U.S. Pat. No. 4,659,558. The unswollen hydrogel is swallowed and in the presence of fluids in the stomach, swells so that the hydrogel is retained within the stomach. The coated pills are released as the hydrogel degrades.

Preferred methods of administration of compositions comprising combinations of at least two or more agents in a single administrative dose include oral routes. The compositions of the present invention can be contained in a gelatin capsule, tablet, liquid or powder, and such items may be coated for ease of swallowing. For oral administration, fine powders or granules may contain diluting, dispersing, and or surface therapeutic agents and may be present in water or in a syrup, in capsules or sachets in the dry state, or in a nonaqueous solution or suspension wherein suspending agents may be included, in tablets wherein binders and lubricants may be included or in a suspension in water or a syrup. Components that may be added such as flavoring, preserving, suspending, thickening or emulsifying agents. Such preparations are known or apparent to those skilled in the art.

One aspect of the present invention comprises methods of treatment of upper respiratory indications such as cough, cold, cold-like symptoms, symptoms related to upper respiratory infections, influenza symptoms, allergic rhinitis, nasal congestion and Eustachian tube congestion comprising administration of compositions comprising a combination of at least two or more therapeutic agents in a single administrative dose through oral delivery compositions and devices. Oral administration includes, but is not limited to, administration through the mucosa of the mouth and any other surfaces of the alimentary canal, stomach, and the gastrointestinal tract. Oral delivery methods are often limited by chemical and physical barriers imposed by the body, such as the varying pH in the gastrointestinal tract, exposure to enzymes and the impermeability of the gastrointestinal membranes. Methods of the present invention for orally administering multi-agent compositions may also include the coadministration of adjuvants with the compositions of the present invention. For example, resorcinols and nonionic surfactants such as polyoxyethylene oleyl ether and n-hexadecyl polyethylene ether, can be administered with or incorporated into the compositions of the present invention to artificially increase the permeability of the intestinal walls. Other methods include the coadministration of enzymatic inhibitors with the compositions of the present invention. Liposomes and emulsions are also contemplated in the present invention for delivery of the compositions.

Methods of treatment of the present invention comprise administration of compositions comprising combinations of at least two or more therapeutic agents in a single administrative dose using microspheres of artificial polymers or proteins that are used for delivery of compositions through various routes, such as gastrointestinal or nasal. Nasal delivery is considered an efficacious route of administration for treatment of upper respiratory indications because the nose has a large surface area available for agent absorption due to the coverage of the epithelial surface by numerous microvilli and the subepithelial layer is highly vascularized. The venous blood from the nose passes directly into the systemic circulation and avoids the loss of agent in a first pass metabolism in the liver.

In order to enhance nasal delivery, absorption enhancers can be added to the compositions of the present invention. Bile salts or derivatives such as fusidic acid, or surfactants, especially nonionic surfactants, can be used to modify the properties of the nasal mucosa to enhance uptake. Microspheres can also be used, particularly those that swell in the presence of moisture. Albumin, starch and DEAE-Sephadex microspheres of 40–60 μm in diameter have been used. These same absorption enhancers can be used in the present invention for enhanced absorption across other mucosal surfaces, such as the gastrointestinal tract or the oral cavity.

Other methods of the present invention comprise treatment of upper respiratory indications by administration of effecting agents such as antihistamines, decongestants, cough suppressants and expectorants in compositions comprising combinations of at least two or more agents in a single administrative dose through the buccal and sublingual membranes. Both the buccal and sublingual membranes offer advantages over other routes of administration. For example, compositions administered through the buccal and sublingual routes have a rapid onset of action, reach high levels in the blood, avoid the first-pass effect of hepatic metabolism and avoid exposure of the multi-agent composition to fluids of the gastrointestinal tract. Additional advantages include easy access to the membrane sites so that the multi-agent compositions can be applied, localized and removed easily. Further, there is good potential for prolonged delivery through the buccal membrane. Administration through the buccal mucosa may be better accepted than rectal dosing and generally avoids local toxic effects, such as has been a problem in nasal administration.

The sublingual mucosa includes the membrane of the ventral surface of the tongue and the floor of the mouth, whereas the buccal mucosa constitutes the lining of the cheek and lips. The sublingual mucosa is relatively permeable, thus giving rapid absorption and acceptable bioavailabilities of many agents. Further the sublingual mucosa is convenient, easily accessible, and generally well accepted. This route has been a traditional route of administration of nitroglycerin and also buprenorphine and nifedipine. The sublingual mucosa is not well suited to sustained-delivery systems because it lacks an expanse of smooth and relatively immobile mucosa suitable for attachment of a retentive delivery system.

Solutes that facilitate the transport of solutes across biological membranes, known as penetration or permeation enhancers, are well known in the art for administering agents. Such compositions are contemplated by the present invention as members of embodiments of the multi-agent compositions. Penetration enhancers can be categorized as chelators, e.g., EDTA, citric acid, and salicylates; surfactants, such as sodium dodecyl sulfate (SDS); non-surfactants, e.g., unsaturated cyclic ureas; bile salts, e.g., sodium deoxycholate, sodium taurocholate; and fatty acids e.g., oleic acid, acylcamitines, mono- and diglycerides.

Penetration enhancers are effective in facilitating mucosal agent administration. For an enhancer to work effectively, the enhancer and multi-agent composition combination is held in position against mucosal tissues for a period of time sufficient to allow enhancer-assisted penetration of the ACE inhibitors, loop diuretics and spironolactone multi-agent composition across the mucosal membrane. In transdermal and transmucosal technology, this is often accomplished by means of a patch or other device that adheres to the skin layer by means of an adhesive.

One of the agents that can be included in the pharmaceutical composition is a permeation enhancer. A permeation enhancer allows for more penetration of the therapeutic agents through the mucous membranes of the body. Permeation enhancers may also be incorporated in transdermal delivery systems. A permeation enhancer is preferably a member selected from the group consisting of cell envelope disordering compounds, solvents, steroidal detergents, bile salts, chelators, surfactants, non-surfactants, fatty acids, and mixtures thereof. A preferred organic solvent is a member selected from the group consisting of a C, or C3 alcohol, and C3 or C4 diol, DMSO, DMA, DMF, 1-n-dodecylcyclazacyclo-heptan-2-one, N-methyl pyrrolidone, N-(2hydroxyethyl) pyrrolidone, triacetin, propylene carbonate and dimethyl isosorbide and mixtures thereof. A preferred cell-envelope disordering compound is a member selected from the group consisting of isopropyl myristate, methyl laurate, oleic acid, oleyl alcohol, glycerol monoleate, glycerol dioleate, glycerol trioleate, glycerol monostearate, glycerol monolaurate, propylene glycol monolaurate, sodium dodecyl sulfate, and sorbitan esters and mixtures thereof. A preferred bile salt is a steroidal detergent selected from the group consisting of natural and synthetic salts of cholanic acid and mixtures thereof.

Oral adhesives are well known in the art. These adhesives consist of a matrix of a hydrophilic, water soluble or swellable, polymer or mixture of polymers that can adhere to a wet mucous surface. These adhesives may be formulated as ointments, thin films, tablets, troches, and other forms. These adhesives may have multi-agent compositions mixed therewith to effectuate slow release or local delivery of a multi-agent composition. Some have been formulated to permit absorption through the mucosa into the circulatory system of the individual.

Another delivery system that is contemplated by the present invention is the controlled released system. The benefits of controlled release delivery systems for delivery of the compositions of the present invention are significant, and provide for reduction in the number of doses and steady drug levels in the blood. One type of agent delivery system comprises using compositions that remain in the stomach over a prolonged period of time. The agent delivery system remains in the stomach and acts as an in vivo reservoir that releases agent at a controlled rate and continuously for absorption in the stomach or for passage to the intestines for absorption. Often the agent is administered from a delivery system that releases a agent as the system moves through the gastrointestinal tract over time. These systems eliminate the need for administering a number of single doses at periodic intervals. This system also provides the advantage of continuously supplying agents so that the blood levels of the agent are controlled and remains at an optimum level.

In controlled release systems contemplated in the present invention, after oral ingestion, agents are released by diffusion and erosion throughout the gastrointestinal tract to a significant degree. Methods of the present invention for the prolongation of gastric retention time, include incorporation of fatty acids to reduce physiological gastric emptying and the use of bioadhesive polymers. Such systems are known to those skilled in the art and comprise using polymers such as polycarbophyll, sodium carboxymethylcellulose, tragacanth gum, acrylates and methacrylates, modified celluloses and polysaccharide gums.

Another delivery system that is contemplated by the present invention for targeting agents to the stomach while avoiding gastric emptying is known as a hydrodynamically balanced system. This system is based on capsules or tablets with bulk density lower than gastric fluid. Thus, the dosage form stays buoyant in the stomach. These dosage forms are comprised of 20–75% of one or more hydrocolloids, e.g., hydroxyethylcellulose and hydroxypropylmethylcellulose.

Other types of these devices include osmotic pressure compartments containing osmotically active salts. In the present invention, dissolution of these salts by the gastric fluid pumps out the therapeutic multi-agent composition. Others are based upon a floating bilayer compressed matrix. One of the layers is comprised of a hydrophilic polymer and a carbon dioxide generating composition. The carbon dioxide maintains buoyancy and the other hydrophilic layer releases the agent from the matrix. A further method for gastric agent targeting involves an intragastric retention shape, made of polyethylene or polyethylene blend. The delivery systems described above may also be used in the present invention to target multi-agent compositions to the upper small intestine. However targeting to other areas of the small intestine may involve several additional systems.

The low stomach pH and presence of gastric enzymes have led to the development of enteric coating. This coating protects the gastric mucosa from agent irritation. Coating is done with a selectively insoluble substance, and protects agents from inactivation by gastric enzymes and/or low pH. The most common enteric coatings are methacrylic acid copolymers, cellulose acetate phthalate, cellulose acetate succinate, and styrol maleic acid copolymers. The most significant drawback of enteric coating is the variability in gastric emptying time. This results in a large variance in blood agent levels.

Another method of drug delivery in the small intestine comprises delivery systems that allow for agent absorption via the lymphatic system. Capillary and lymphatic vessels are permeable to lipid-soluble compounds and low molecular weight moieties. Another approach for targeting agents to the small intestine involves the use of intestinal sorption promoters. Such promoters include long chain fatty acids, including linoleic acid, acylcamitines, and palmitocarnitine. Bioadhesives can also be used in the present invention to prolong intestinal transit, as in buccal delivery systems. The adhesion to the intestinal mucosa takes place either by mechanical interlocking or other mechanisms.

A preferred tablet for oral administration in the methods of the resent invention, preferably for buccal delivery systems, comprises an adhesive layer comprising a hydrophilic polymer with one surface adapted to contact a first tissue of the oral cavity and adhere thereto when wet and an opposing surface in contact with and adhering to an adjacent agent/enhancer layer comprising a permeation enhancer and multi-agent composition. The agent/enhancer layer contacts and is in agent transfer relationship with the buccal mucosa when the adhesive layer contacts and adheres to the first tissue, preferably the gingiva. Preferably the hydrophilic polymer comprises compounds selected from the group consisting of hydroxypropyl cellulose, hydroxypropyl methylcellulose, hydroxyethylcellulose, ethylcellulose, carboxymethyl cellulose, dextran, guar-gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and mixtures thereof. The adhesive layer may additionally contain one or more members selected from the group consisting of fillers, tableting excipients, lubricants, flavors, and dyes and that the agent/enhancer layer additionally contain one or members selected from the group consisting of tableting excipients, fillers, flavors, taste-masking agents, dyes, stabilizers, enzyme inhibitors, and lubricants.

The present invention comprises methods of administration of compositions comprising combinations of at least two or more agents in a single administrative dose in transdermal delivery systems for the treatment of upper respiratory symptoms. Transdermal methods provide methods of administration that have high patient compliance. The present invention comprises methods of treating upper respiratory symptoms that include transdermal patches or assisted transdermal delivery such as with electricity or ultrasound.

Transdermal drug delivery (TDD) offers several advantages over traditional delivery methods including injections and oral delivery. When compared to oral delivery, TDD avoids gastrointestinal agent metabolism, reduces first-pass liver metabolism effects, and provides sustained release of multi-agent compositions. In actuality, transdermal delivery is the transport of therapeutic compositions across the epidermis where the compositions get absorbed in the blood capillaries. When compared to injections, TDD eliminates the associated pain and the possibility of infection. The transdermal route of administration provides an alternative method and avoids gastrointestinal degradation and gastrointestinal uptake problems.

One detriment of transdermal delivery of therapeutic compositions is the low permeability of skin. This low permeability is attributed to the stratum corneum, the outermost skin layer which consists of dead cells and keratin fibers, keratinocytes, surrounded by lipid bilayers. The highly ordered structure of the lipid bilayers confers an impermeable character to the skin. The transdermal methods of the present invention include compositions of chemical, permeation or penetration enhancers and and methods of applying electricity or ultrasound to enhance transdermal multi-agent composition transport.

Ultrasound has been shown to enhance transdermal transport of agents (molecular weight less than 500) across human skin, a phenomenon referred to as sonophoresis. It has been shown that application of ultrasound at therapeutic frequencies (1 MHz) induces growth and oscillations of air pockets present in the keratinocytes of the skin in a process known as cavitation. These oscillations disorganize the skin lipid bilayers and enhance transdermal transport.

Transdermal agent delivery offers an advantageous alternative to oral delivery and injections. A variety of delivery systems can be used to enhance transdermal transport of agents. These include use of chemicals to either modify the skin structure or to increase the agent concentration in the transdermal patch; ii) applications of electric fields to create transient transport pathways, such as electroporation, or to increase the mobility of charged agents through the skin, such as in iontophoresis, and application of ultrasound, sonophoresis. U.S. Pat. No. 4,309,989 to Fahim and U.S. Pat. No. 4,767,402 to Kost, et al., disclose various ways in which ultrasound has been used to aehieve transdermal agent delivery.

The present invention contemplates the administration of multi-agent compositions provided in a single administrative dose using sonophoresis. Although a variety of ultrasound conditions have been used for sonophoresis, the most commonly used conditions correspond to the therapeutic ultrasound having frequency in the range of 1 MHz–MHz and intensity in the range of 0–2 W/cm$^2$. An optimal selection of ultrasound parameters, such as frequency, pulse length, intensity, as well as of nonultrasonic parameters, such as ultrasound coupling medium, can be conducted to ensure a safe and effeicacious application using the methods known in the art, such as are taught in U.S. Pat. No. 5,814,599, included herein in its entirety. For example, a preferred delivery method of the present invention uses ultrasound at a frequency of between 20 kHz and 10 kHz at an intensity that does not cause irreversible skin damage for a period of time effective to deliver the agent.

As used herein, sonophoresis is the application of ultrasound to the skin on which a multi-agent composition, alone or in combination with a carrier, penetration enhancer, lubricant, or other pharmaceutically acceptable agent for application to the skin, has been applied. Ultrasound is defined as sound at a frequency of between 20 kHz and 10 MHz, with intensities of between greater than 0 and 3 W/cm$^2$. As used herein, "low frequency" sonophoresis is ultrasound at a frequency that is less than 1 MHz, more typically in the range of 20 to 40 kHz, which is preferably applied in pulses, for example, 100 msec pulses every second at intensities in the range of between zero and 1 W/cm$^2$, more typically between 12.5 mW/cm$^2$ and 225 mW/cm$^2$. Exposures are typically for between 1 and 10 minutes, but may be shorter and/or pulsed. The intensity should not be so high as to raise the skin temperature more than about one to two degrees Centigrade.

Many ultrasound devices are available commercially which can be used in the present invention. For example, the ultrasonic devices used by dentists to clean teeth have a frequency of between about 25 and 40 kHz. Commercially available portable ultrasound toothbrushes make use of a small sonicator contained within the toothbrush. This sonicator is portable and operates on rechargeable batteries. Small pocket-size sonicators carried by patients and used to "inject" a therapeutic composition whenever required could be readily adapted from these devices.

The present invention comprises methods of treatment of upper respiratory symptoms comprising administering effective amounts of compositions comprising combinations two or more therapeutic agents comprising antihitamines, decongestants, antitussives and expectorants in a single administrative dose. Not all methods of administration are efficacious for every patient. Therefore, the present invention comprises methods of delivery of differing formulations of the antihitamines, decongestants, antitussives and expectorants as multi-agent compositions provided in single administrative doses. The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the therapeutic ingredient and the pharmaceutical carrier(s) or excipient(s). In general, the formulations are prepared by uniformly and intimately bringing into associate the therapeutic ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the therapeutic ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the therapeutic ingredient in a free-flowing form such as a powder or granules, optionally mixed with a binder, lubricant, inert diluent, preservative, surface therapeutic or dispersing agent. Molded tablets may be made by molding, in a suitable machine, a mixture of the powdered compound moistened with an inert liquid diluent. The tablets may be optionally coated or scored and may be formulated so as to provide a slow or controlled release of the therapeutic ingredient therein.

Formulations suitable for topical administration in the mouth include lozenges comprising the ingredients in a flavored basis, usually sucrose and acacia or tragacanth; pastilles comprising the therapeutic ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the therapeutic ingredient.

Formulations suitable for vaginal administration may be presented as pessaries, tamports, creams, gels, pastes, foams or spray formulations containing in addition to the therapeutic ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents. Many variations of the present invention may suggest themselves to those skilled in the art in light of the above detailed disclosure. All such modifications are within the full intended scope of the appended claims.

What is claimed is:

1. A liquid suspension for treating upper respiratory indications comprising pseudoephedrine tannate, chlorpheniramine tannate and dextromethorphan tannate, wherein the concentration of pseudoephedrine tannate in the composition is 75–300 mg per 5 mL, the concentration of chlorpheniramine tannate in the composition is 4–6 mg per 5 mL, and the concentration of dextromethorphan tannate in the composition is 10–30 mg per 5 mL.

2. The liquid suspension of claim 1, wherein the concentration of pseudoephedrine tannate in the composition is 75 mg per 5 mL and the concentration of chlorpheniramine tannate in the composition is 4.5 mg per 5 mL.

3. A liquid suspension for treating upper respiratory indications comprising dexchlorpheniramine tannate and pseudoephedrine tannate.

4. The liquid suspension of claim 3, further comprising dextromethorphan tannate.

* * * * *

UNITED STATES PATENT AND TRADEMARK OFFICE
CERTIFICATE OF CORRECTION

PATENT NO. : 6,509,492 B1  
DATED : January 21, 2003  
INVENTOR(S) : Venkataraman It is certified that error appears in the above-identified patent and that said Letters Patent is hereby corrected as shown below:

Column 1,  
Line 43, "dcongestants" should read -- decongestants --.

Column 7,  
Line 58, insert the following two paragraphs:

--The present invention further comprises compositions comprising chiral compositions such as, but not limited to, dextromethorphane tannate, dexchlorpheniramine tannate, and dexbrompheniramine tannate. Enzymes and receptors are designed to accept single chiral configurations such as L-amino acids or D-sugars. It is therefore thought that different enantiomers have different pharmacokinetics and therefore different biological activity. Scientific advances in stereochemistry now permit the production of single isomers separating compounds such as methorphane, chlopheniramine and brompheniramine into dextromethorphane, dexchlopheniramine and dexbrompheniramine. The methods of separating a racemic mixture into the sterioisomers are well known in the art.

Generally, only one isomer of a compound has the therapeutic activity sought, though both isomers may have biological activity. The other isomer may aid in the function of the therapeutic isomer, it may have it's own therapeutic effects, it may be inert, it may contribute to side effects or decreased efficacy of a drug due to dilution of the final product, or it may contribute to toxicity. The therapeutically non active isomer can be viewed as an impurity at best, and in the worse case, the enantiomer is the agent of intolerable side effects. The creation of singly enantiomeric forms of a drug can therefore contribute to increased efficacy and lower required dosages with fewer side effects.--

Column 12,  
Line 11, "tubes Mucosal" should read -- tubes. Mucosal --.

Column 16,  
Line 38, "resent" should read -- present --.

Signed and Sealed this

First Day of July, 2003

JAMES E. ROGAN  
*Director of the United States Patent and Trademark Office*